(12) United States Patent
Ueda

(10) Patent No.: US 11,065,383 B2
(45) Date of Patent: Jul. 20, 2021

(54) CONNECTOR AND TRANSFUSION SET

(71) Applicant: TERUMO KABUSHIKI KAISHA, Tokyo (JP)

(72) Inventor: Yasuhiro Ueda, Kofu (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 649 days.

(21) Appl. No.: 15/010,562

(22) Filed: Jan. 29, 2016

(65) Prior Publication Data

US 2016/0144110 A1 May 26, 2016

Related U.S. Application Data

(63) Continuation of application No. PCT/JP2014/001747, filed on Mar. 26, 2014.

(30) Foreign Application Priority Data

Jul. 31, 2013 (JP) .............................. JP2013-159894

(51) Int. Cl.
*A61M 5/168* (2006.01)
*A61M 39/22* (2006.01)
(Continued)

(52) U.S. Cl.
CPC ...... *A61M 5/16813* (2013.01); *A61M 5/1413* (2013.01); *A61M 39/10* (2013.01);
(Continued)

(58) Field of Classification Search
CPC .......... A61M 2039/229; A61M 39/223; A61M 39/26; A61M 39/04; A61M 39/045;
(Continued)

(56) References Cited

U.S. PATENT DOCUMENTS 2,538,662 A * 1/1951 Abbott .................. A61M 5/158
604/247
4,712,583 A * 12/1987 Pelmulder ............. A61M 39/24
137/494

(Continued)

FOREIGN PATENT DOCUMENTS

CN 203763665 U 8/2014
CN 104080507 A 10/2014
(Continued)

OTHER PUBLICATIONS

The extended European Search Report dated Feb. 20, 2017, by the European Patent Office in corresponding European Patent Application No. 14831873.6 (8 pgs).
(Continued)

*Primary Examiner* — Brandy S Lee
*Assistant Examiner* — Hong-Van N Trinh
(74) *Attorney, Agent, or Firm* — Buchanan Ingersoll & Rooney PC

(57) ABSTRACT

A connector provided with a housing which defines an insertion section into which a male connector is inserted from the outside and a flow path communicating with the insertion section and an elastic valve body which has a slit and blocks the insertion section. The housing includes a tip receiving section formed on an inner wall defining the flow path, the tip receiving section receiving a tip of the male connector inserted through the slit of the elastic valve body. The tip receiving section is formed on only a part of the inner wall in a cross section that is perpendicular to an insertion direction of the male connector and includes at least a part of the tip receiving section.

18 Claims, 14 Drawing Sheets

(51) Int. Cl.
*A61M 5/14* (2006.01)
*A61M 39/10* (2006.01)
*A61M 39/24* (2006.01)

(52) U.S. Cl.
CPC ... *A61M 39/223* (2013.01); *A61M 2039/1072* (2013.01); *A61M 2039/1077* (2013.01); *A61M 2039/1083* (2013.01); *A61M 2039/1088* (2013.01); *A61M 2039/229* (2013.01); *A61M 2039/2426* (2013.01)

(58) Field of Classification Search
CPC .. A61M 2039/2426; A61M 2039/1083; A61M 2039/1088; A61M 2039/1077; A61M 2039/1072; A61M 39/10; A61M 5/16813; A61M 5/1413; A61M 2039/0036; A61M 2039/1033
See application file for complete search history.

(56) References Cited

U.S. PATENT DOCUMENTS

| | | | |
|---|---|---|---|
| 5,203,943 | A | 4/1993 | Nornberg et al. |
| 6,003,553 | A * | 12/1999 | Wahlberg .............. A61M 39/10 137/625.47 |
| 6,468,251 | B1 | 10/2002 | Yamanaka et al. |
| 2003/0109853 | A1* | 6/2003 | Harding .............. A61M 39/045 604/536 |
| 2005/0159710 | A1* | 7/2005 | Utterberg .............. A61M 39/02 604/256 |
| 2006/0184140 | A1* | 8/2006 | Okiyama ............ A61M 39/045 604/249 |
| 2009/0084446 | A1 | 4/2009 | Kitani |
| 2010/0063440 | A1* | 3/2010 | Kitani .................. A61M 39/045 604/83 |
| 2011/0233435 | A1 | 9/2011 | Matsumoto et al. |
| 2011/0306940 | A1 | 12/2011 | Miyasaka |
| 2011/0308651 | A1* | 12/2011 | Ziv .................... A61M 39/223 137/625.46 |
| 2014/0018746 | A1 | 1/2014 | Ueda et al. |
| 2014/0332091 | A1 | 11/2014 | Ueda et al. |
| 2015/0297880 | A1 | 10/2015 | Ogawa et al. |
| 2017/0106182 | A1 | 4/2017 | Yoshioka et al. |

FOREIGN PATENT DOCUMENTS

| | | |
|---|---|---|
| CN | 104640596 A | 5/2015 |
| JP | 04-292176 | 10/1992 |
| JP | 3389983 | 7/1999 |
| JP | 2008-511371 | 4/2008 |
| JP | 2012-000117 | 1/2012 |
| JP | 2012-071162 | 4/2012 |
| WO | WO 2006-025054 | 3/2006 |
| WO | 2012/133100 A1 | 10/2012 |
| WO | 2012/133131 A1 | 10/2012 |
| WO | 2013/115293 A1 | 8/2013 |
| WO | 2015/156272 A1 | 10/2015 |

OTHER PUBLICATIONS

Office Action (The First Office Action) dated Jun. 15, 2018, by the State Intellectual Property Office (SIPO) of the People's Republic of China in corresponding Chinese Patent Application No. 201480042795.0 and an English Translation of the Office Action. (18 pages).
Office Action (The Second Office Action) dated Mar. 5, 2019, by the State Intellectual Property Office (SIPO) of the People's Republic of China in corresponding Chinese Patent Application No. 201480042795.0 and an English Translation of the Office Action. (11 pages).

* cited by examiner

CONNECTOR AND TRANSFUSION SET

CROSS-REFERENCE TO RELATED APPLICATION

This application is a continuation of International Application No. PCT/JP2014/001747 filed on Mar. 26, 2014, the entire content of which is incorporated herein by reference.

TECHNICAL FIELD

The disclosure herein relates to a connector and an infusion set. In particular, the disclosure relates to a connector that is capable of connecting thereto a male connector such as various medical devices and infusion solution containers and an infusion set provided with the connector.

BACKGROUND DISCUSSION

Conventionally, when infusion, blood transfusion, or artificial dialysis is performed, liquid is fed into the body using a medical tube. When another liquid such as a liquid medicine is joined to the liquid inside the tube, a connector that is capable of liquid-tightly connecting a male connector such as a syringe and a luer taper member to the medical tube is used. A male connector such as a syringe and a luer taper member may be called a male luer, and a connector connected to the male luer may be called a female luer.

Such a connector capable of connecting a male connector is disclosed, for example, in JP 3389983 B2. Specifically, JP 3389983 B2 discloses a mixed injection port as a connector that includes a disc-like valve which has an insertion hole formed on a central part thereof, a base which supports the lower part of the peripheral edge of the valve excepting the central part of a back side face of the valve, and a cover which covers at least the upper part of the peripheral edge of the valve excepting the central part of a front side face of the valve to fixedly support the valve.

Further, JP 3389983 B2 discloses a cover which has a circular fitting hole formed in the center thereof. When an insertion body such as a male connector is inserted, the edge of the cover forming the fitting hole serves as locking means for locking the insertion body and the insertion body is locked by the insertion hole of the valve and the fitting hole of the cover.

However, in the above mixed injection port in JP 3389983 B2, the insertion length of the insertion body such as a male connector may be increased by a user. In this case, a large load may be disadvantageously applied to the vale and the cover.

SUMMARY

In view of the above, the disclosure here provides a connector capable of preventing a male connector from being excessively inserted into the connector and an infusion set provided with the connector.

A connector according to a first aspect of the disclosure includes a housing defining an insertion section into which a male connector is inserted from the outside and a flow path communicating with the insertion section and an elastic valve body having a slit and blocking the insertion section. The housing includes a tip receiving section formed on an inner wall defining the flow path, the tip receiving section receiving a tip of the male connector inserted through the slit of the elastic valve body. The tip receiving section is formed only on a part of the inner wall in a cross section that is perpendicular to an insertion direction of the male connector and includes at least a part of the tip receiving section.

As an exemplary embodiment of the disclosure, preferably, the tip receiving section is adjacent to the flow path in the cross section.

As a further exemplary embodiment of the disclosure, preferably, the tip receiving section includes projections projecting toward the flow path in a direction perpendicular to the insertion direction.

As an exemplary embodiment of the disclosure, preferably, a tip receiving face of each of the projections, the tip receiving face receiving the tip of the male connector, has an extending section extending in such a manner that a projecting amount toward the flow path in the direction perpendicular to the insertion direction increases toward the insertion direction.

As an exemplary embodiment of the disclosure, preferably, each of the projections becomes gradually slimmer from a base toward an apex when viewed in the insertion direction.

As a further exemplary embodiment of the disclosure, preferably, the projections face each other across the flow path in the direction perpendicular to the insertion direction.

As an exemplary embodiment of the disclosure, preferably, the inner wall includes the projections and a circular arc section continuous on both sides of each of the projections in the cross section.

As an exemplary embodiment of the disclosure, preferably, the housing includes a branch port holding the elastic valve body and defining the flow path, and an upstream port located on one side and a downstream port located on the other side with the flow path interposed therebetween in a direction perpendicular to the insertion direction of the male connector. Further, when the flow path is defined as a first flow path, the upstream port defines a substantially cylindrical second flow path communicating with the first flow path and the downstream port defines a substantially cylindrical third flow path communicating with the first flow path.

As an exemplary embodiment of the disclosure, preferably, the housing includes a substantially cylindrical holder main body, and a cock defining a hollow section together with an inner wall of the holder main body is rotatably housed inside the holder main body. Further, when the flow path is defined as a first flow path, a branch port holding the elastic valve body and defining the first flow path communicatable with the hollow section, an upstream port defining a substantially cylindrical second flow path communicatable with the hollow section, and a downstream port defining a substantially cylindrical third flow path communicatable with the hollow section are disposed on an outer wall of the holder main body. Further, the connector is capable of supplying liquid flowing in the second flow path to the third flow path through the hollow section and the first flow path.

As a further exemplary embodiment of the disclosure, preferably, the housing includes a partition wall dividing the flow path defined by the branch port into two flow paths in the direction perpendicular to the insertion direction of the male connector inserted into the branch port, and the tip of the male connector and the partition wall are not in contact with each other when the tip receiving section receives the tip of the male connector.

As an exemplary embodiment of the disclosure, preferably, the tip receiving section receives the tip of the male connector through the elastic valve body.

A second aspect of the disclosure herein is directed to an infusion set provided with the connector.

The connector and the infusion set provided with the connector of the disclosure make it possible to prevent the insertion length of a male connector from being excessively increased when the male connector is inserted.

DETAILED DESCRIPTION

Hereinbelow, exemplary embodiments of a connector and an infusion set according to the disclosure will be described with reference to FIGS. 1(A) to 13. Common members are denoted by identical reference signs throughout the drawings.

Figure 1A:
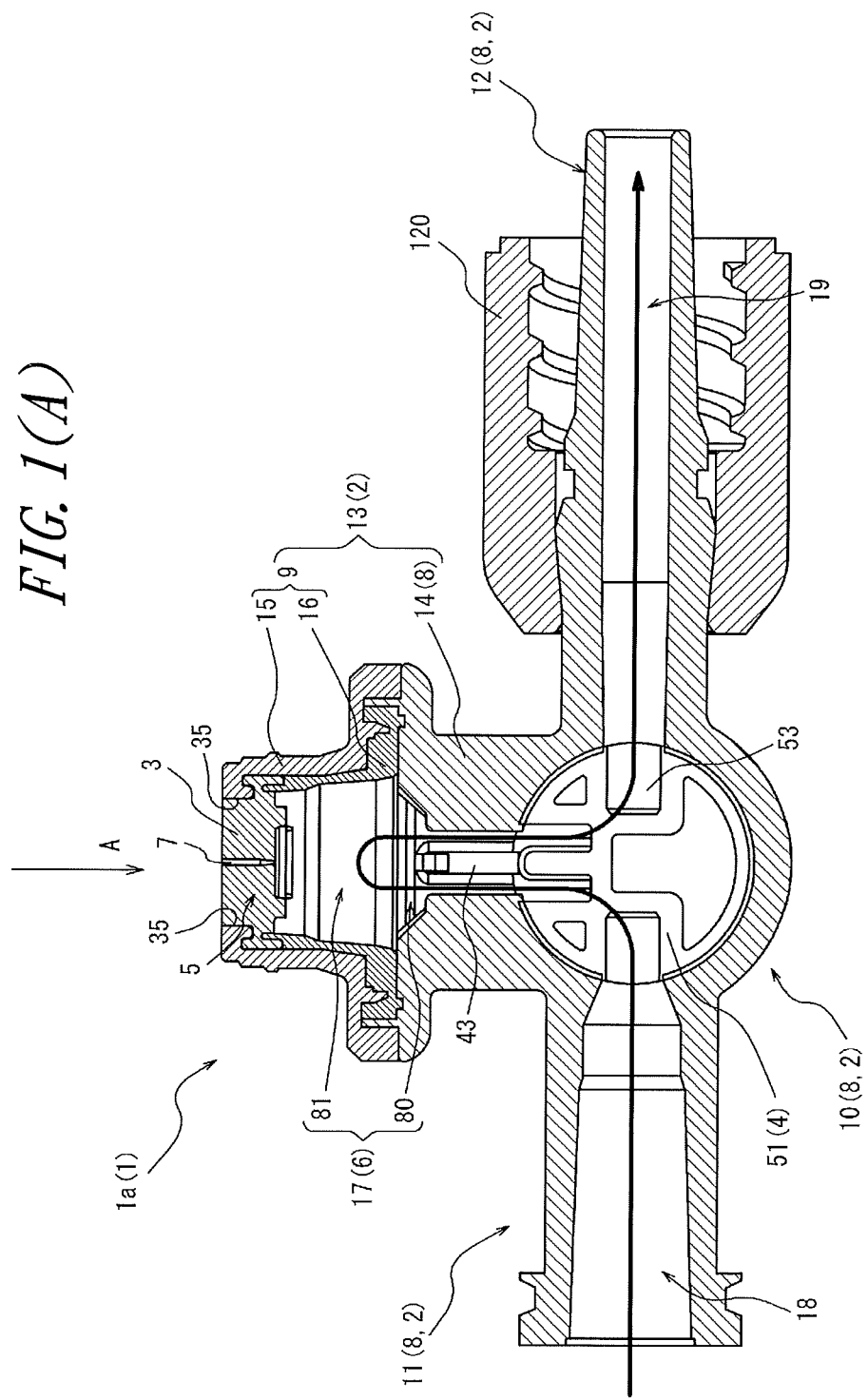
FIG. 1(A) is a sectional view of a connector according to an exemplary embodiment of the disclosure.
Figure 1B:
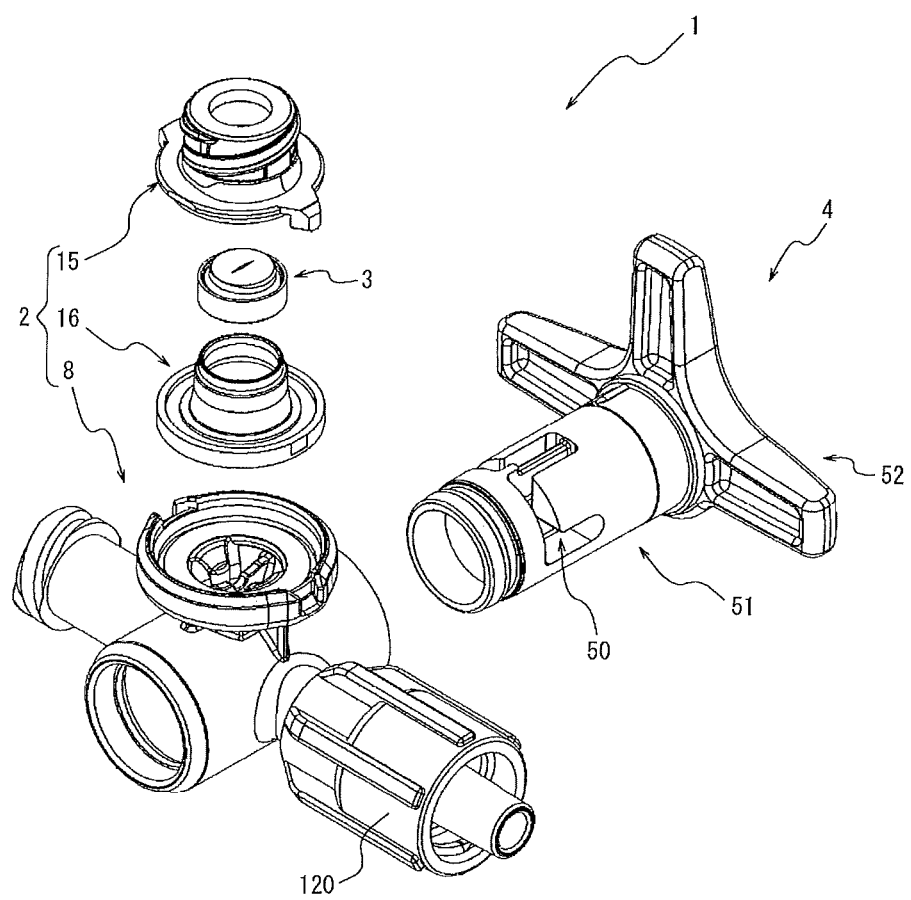
FIG. 1(B) is an exploded perspective view of the connector shown in FIG. 1(A).

First, one exemplary embodiment of the connector according to the disclosure here will be described. FIG. 1(A) is a sectional view illustrating a three-way stopcock 1a as a connector 1 in the exemplary embodiment. FIG. 1(B) is an exploded perspective view of the three-way stopcock 1a.

As illustrated in FIGS. 1(A) and 1(B), the connector 1 is provided with a housing 2, an elastic valve body 3 which is attached to the housing 2, and a cock 4 which is housed inside the housing 2.

As illustrated in FIGS. 1(A) and 1(B), the housing 2 defines an insertion section 5 into which a male connector 100 (refer to FIG. 11) is inserted from the outside and a flow path 6 which communicates with the insertion section 5 in an insertion direction A of the male connector 100. The elastic valve body 3 has a slit 7 so that the elastic valve body 3 elastically deforms to open or close the slit 7 when the male connector 100 is attached to or detached from the connector 1. The elastic valve body 3 blocks the insertion section 5 defined by the housing 2. The insertion section 5 of the housing 2 is a space in which the elastic body 3 is located when the male connector 100 is not inserted. Thus, the flow path 6 of the housing 2 is located on an inner side with respect to the elastic valve body 3 in this state. The "communication" between the insertion section 5 and the flow path 6 means connection between the spaces, and includes not only direct connection between the spaces, but also connection between the spaces through another space.

Specifically, the housing 2 in the present exemplary embodiment is provided with a holder 8 and a cap 9. The holder 8 is provided with a substantially cylindrical holder main body 10 which houses the cock 4 inside thereof, an upstream port 11 which is disposed on an outer wall of the holder main body 10, a downstream port 12 which is disposed on the outer wall of the holder main body 10 at a position opposite to the upstream port 11 across the holder main body 10, and a cap support section 14 which is disposed on the outer wall of the holder main body 10, constitutes a branch port 13 together with the cap 9, and supports the cap 9. A substantially cylindrical lock connector 120 which has a screw thread formed on the inner peripheral face thereof is attached to the outer periphery of the substantially cylindrical downstream port 12 illustrated in FIGS. 1(A) and 1(B) and used for connecting the downstream port 12 to another connector.

In the exemplary embodiment, the branch port 13 of the housing 2 defines the insertion section 5 and the flow path 6. The cap 9 which defines the insertion section 5 holds the elastic valve body 3 so that the elastic valve body 3 blocks the insertion section 5. More specifically, the cap 9 includes a top face cap 15 and a bottom face cap 16. The insertion section 5 is defined by a part of an inner wall of the top face cap 15 and a part of an inner wall of the bottom face cap 16. The elastic valve body 3 is held between the top face cap 15 and the bottom face cap 16 so that the elastic valve body 3 is held inside the insertion section 5 and the position thereof is fixed. The flow path 6 in the present embodiment is defined by the bottom face cap 16 and the cap support section 14.

As indicated by an arrow in FIG. 1(A), the holder main body 10 has a function of connecting flow paths defined by the upstream port 11, the downstream port 12, and the branch port 13 with the cock 4 housed inside thereof. Specifically, the cock 4 is provided with a substantially cylindrical flow path switching section 51 which has a groove 50 (refer to FIG. 1(B)) formed on a part of the outer peripheral face thereof and is housed inside the holder main body 10 and a grasping section 52 (refer to FIG. 1(B)) used to make the flow path switching section 51 rotatable inside the holder main body 10. The cock 4 defines a hollow section 53 which connects the flow paths defined by the upstream port 11, the downstream port 12, and the branch port 13 by the inner wall of the holder main body 10 and a groove wall of the groove 50 formed on an outer wall of the flow path switching section 51.

In the present embodiment, in order to distinguish between the flow paths defined by the upstream port 11, the downstream port 12, and the branch port 13, the flow path 6 defined by the branch port 13 is referred to as a first flow path 17, a substantially cylindrical flow path defined by the upstream port 11 is referred to as a second flow path 18, and a substantially cylindrical flow path defined by the downstream port 12 is referred to as a third flow path 19 in the following description.

The cap support section 14 supports the top face cap 15 and the bottom face cap 16 as the cap 9. In the present embodiment, both the top face cap 15 and the bottom face cap 16 have contact with the cap support section 14 so as to be supported by the cap support section 14. Alternatively, the bottom face cap 16 may be held by the top face cap 15, and only the top face cap 15 may be allowed to have contact with the cap support section 14 so as to be supported by cap support section 14. On the contrary, the top face cap 15 may be held by the bottom face cap 16, and only the bottom face cap 16 may be allowed to have contact with the cap support section 14 so as to be supported by the cap support section 14.

Examples of the materials of the holder main body 10, the upstream port 11, the downstream port 12 and the cap support section 14 as the holder 8, and the top face cap 15 and the bottom face cap 16 as the cap 9 all of which together constitute the housing 2 include various resin materials such as polyolefin such as polyethylene, polypropylene, and an ethylene-propylene copolymer; an ethylene-vinyl acetate copolymer (EVA); polyvinyl chloride; polyvinyliden chloride; polystyrene; polyamide; polyimide; polyamide-imide; polycarbonate; poly(4-mehyl-1-pentene); ionomer; an acrylic resin; polymethyl methacrylate; an acrylonitrile-butadiene-styrene copolymer (ABS resin); an acrylonitrile-styrene copolymer (AS resin); a butadiene-styrene copolymer; polyester such as polyethylene terephthalate (PET), polybutylene terephthalate (PBT), and polycyclohexane terephthalate (PCT); polyether; polyether ketone (PEK); polyether ether ketone (PEEK); polyether imide; polyacetal (POM); polyphenylene oxide; modified polyphenylene oxide; polysulfone; polyether sulfone; polyphenylene sulfide; polyarylate; aromatic polyester (a liquid crystal polymer); and polytetrafluoroethylene, polyvinylidene fluoride and other fluororesins. A blend or a polymer alloy containing one or more kinds of the above resin materials may also be used. Alternatively, various glass materials, ceramic materials, or metal materials may be used.

The elastic valve body 3 is molded and formed to be elastically deformable. Examples of the material of the elastic valve body 3 include various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, and fluoro rubber; and various thermoplastic elastomers such as a styrene-based thermoplastic elastomer, a polyolefin-based thermoplastic elastomer, a polyvinyl chloride-based thermoplastic elastomer, a polyurethane-based thermoplastic elastomer, a polyester-based thermoplastic elastomer, a polyamide-based thermoplastic elastomer, a polybutadiene-based thermoplastic elastomer, a transpolyisoprene-based thermoplastic elastomer, a fluoro rubber-based thermoplastic elastomer, and a chlorinated polyethylene-based thermoplastic elastomer. A material mixed with one or two or more kinds of these materials may also be used.

The hardness of the elastic valve body 3 is preferably 20 to 60° (A hardness). Accordingly, a moderate elastic force can be ensured in the elastic valve body 3. Thus, elastic deformation (described below) can be generated in the elastic valve body 3.

The same material as the housing 2 may be used as the materials of the flow path switching section 51 and the grasping section 52 of the cock 4.

Hereinbelow, each member in the present embodiment will be described in detail.

Figure 2A:
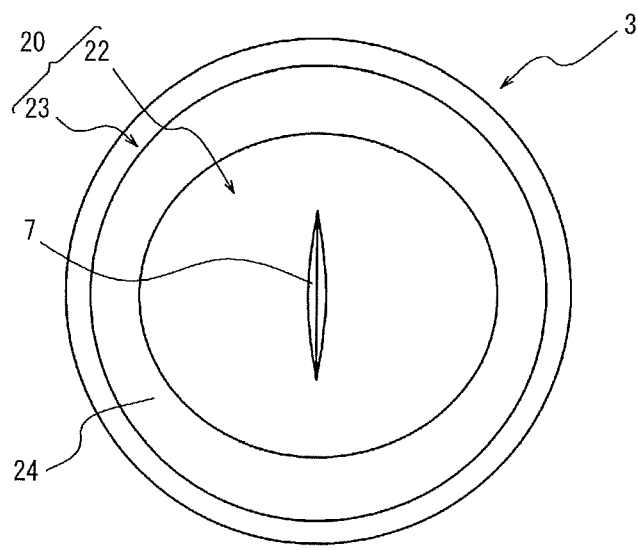
FIG. 2(A) is a diagram illustrating a top face of an elastic valve body used in the connector.
Figure 2B:
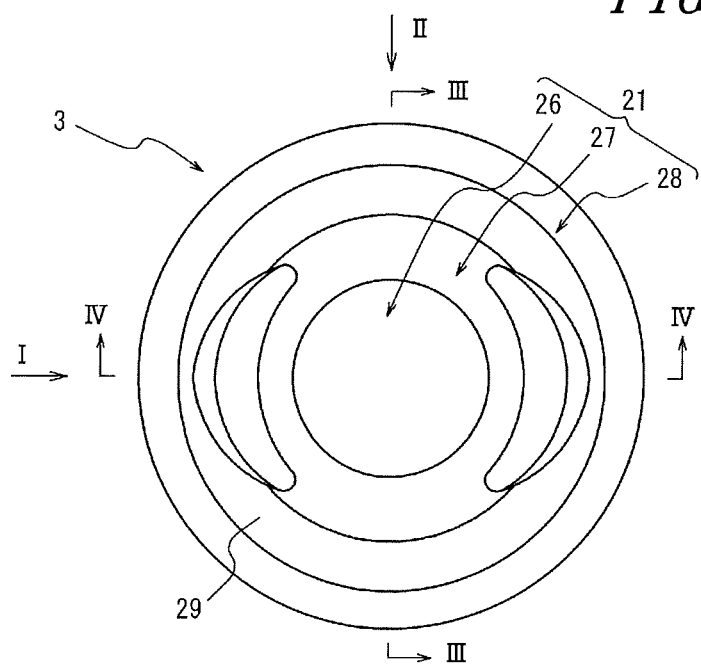
FIG. 2(B) is a diagram illustrating a bottom face of the elastic valve body.
Figure 3A:
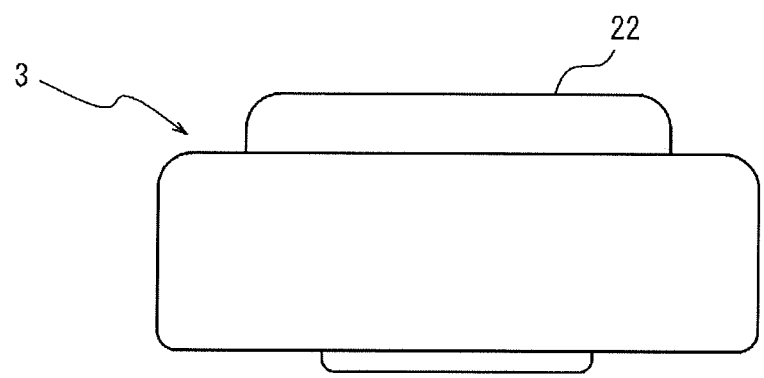
FIG. 3(A) is a side view of the elastic valve body viewed from a direction I of FIG. 2(B)
Figure 3B:
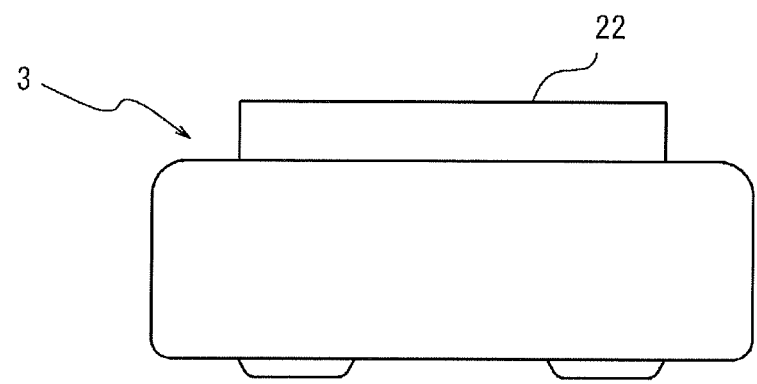
FIG. 3(B) is a side view of the elastic valve body viewed from a direction II of FIG. 2(B).
Figure 4A:
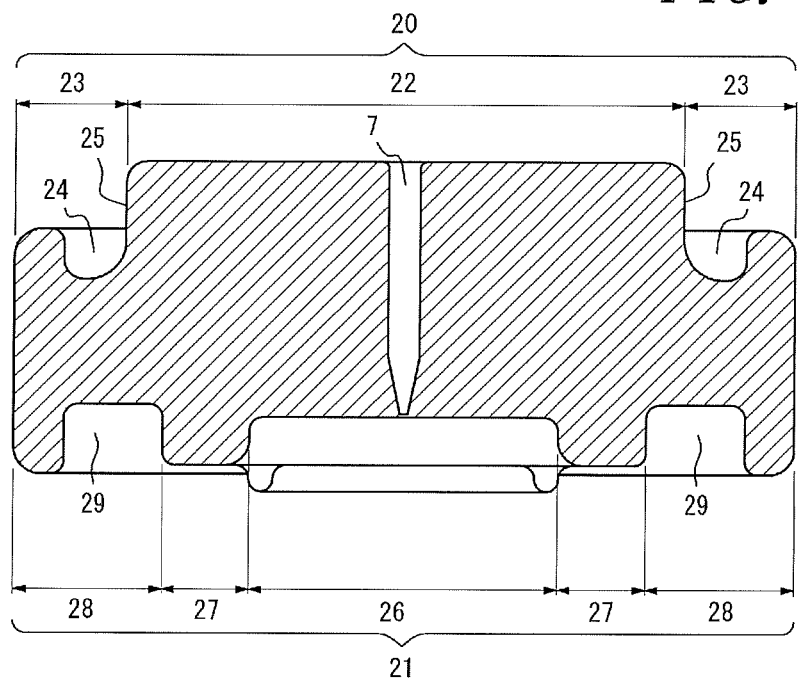
FIG. 4(A) is a sectional view of the elastic valve body taken along line III-III of FIG. 2(B)
Figure 4B:
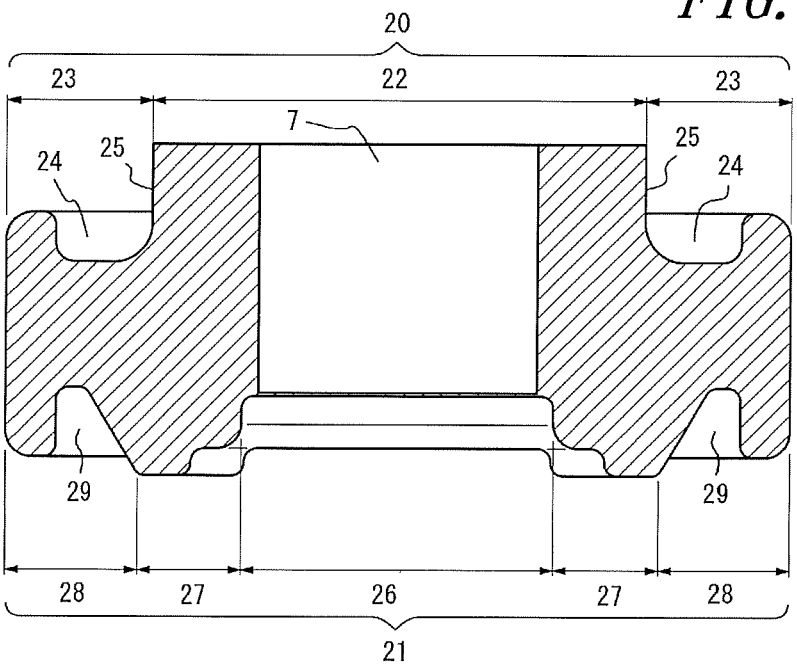
FIG. 4(B) is a sectional view of the elastic valve body taken along line IV-IV of FIG. 2(B).

FIGS. 2(A) and 2(B) are diagrams respectively illustrating a top face 20 and a bottom face 21 of the elastic valve body 3. FIGS. 3(A) and 3(B) are side views of the elastic valve body 3 respectively viewed from the direction of arrows I and II illustrated in FIG. 2(B). FIGS. 4(A) and 4(B) are sectional views of the elastic valve body 3 respectively taken along line III-III and line IV-IV in FIG. 2(B).

As illustrated in FIGS. 2(A) to 4(B), the elastic valve body 3 is a disc-like valve body having a disc-like outer shape. The top face 20 includes a planar top face central region 22 and a top face outer region 23 which is located on the outer side in the radial direction with respect to the top face central region 22. The top face central region 22 has a shape which projects outward (upward in FIGS. 3(A) to 4(B)) with respect to the top face outer region 23. The straight slit 7 is formed on the center of the top face central region 22. The slit 7 is molded. The slit 7 does not penetrate the elastic valve body 3 up to the bottom face 21 when molded, but will penetrate the elastic valve body 3 up to the bottom face 21 when, for example, the male connector 100 (refer to FIG. 11) is first inserted after the molding. A process of allowing the slit 7 to penetrate the elastic valve body 3 may be executed as a part of the manufacturing process after the molding is completed. As illustrated in FIG. 2(A), the top face central region 22 is formed in an elliptical shape having a minor axis in a longitudinal direction (extending direction) of the slit 7 and a major axis in a direction perpendicular to the longitudinal direction of the slit 7 when the elastic valve body 3 is not housed in the insertion section 5 (refer to FIG. 1(A)). When the elastic valve body 3 is housed in the insertion section 5, the ellipse of the top face central region 22 is pushed by an inner wall 35 (refer to FIG. 1(A)) on the major axis side thereof to form a circular shape. Accordingly, inner faces of the slit 7 are brought into intimate contact with each other to close the slit 7. For the purpose of facilitating understanding of the configuration, FIGS. 1(A) and 1(B) and FIGS. 5, 9 and 10 (referred to below) illustrate the slit 7 that is not in an intimate-contact and closed state. As illustrated in FIGS. 4(A) and 4(B), a top face annular groove 24 is formed on the top face outer region 23 in a manner to surround the top face central region 22. A locking projection 34 (refer to FIG. 5, described below) of the top face cap 15 enters the top face annular groove 24 and compresses the elastic valve body 3 to constitute a part of a holding section. In the top face annular groove 24 of the present embodiment, a groove wall adjacent to the top face central region 22 is formed in a circular arc shape in the sectional views of FIGS. 4(A) and 4(B). Such a configuration enables a restoring performance of the elastic valve body 3 to be improved. Although, in the present embodiment, the top face annular groove 24 is formed at a position adjacent to the top face central region 22, that is, a side wall 25 of the top face central region 22 projecting outward in the sectional views of FIGS. 4(A) and 4(B) also constitutes the groove wall of the top face annular groove 24, the position or the shape of the top face annular groove 24 may be appropriately modified in accordance with the position or the shape of the locking projection 34 of the top face cap 15.

The bottom face 21 of the elastic valve body 3, the bottom face 21 being located opposite to the top face 20, includes a planar bottom face central region 26, a thick region 27 which is located on the outer side in the radial direction with respect to the bottom face central region 26, and a bottom face outer region 28 which is located on the outer side in the radial direction with respect to the thick region 27. The slit 7 is not formed on the bottom face central region 26. However, as described above, for example, when the male connector 100 (refer to FIG. 11) is first inserted, a part located between the tip of the slit 7 formed on the top face 20 and the bottom face central region 26 is split, which allows the slit 7 to communicate with the top face central region 22 through the bottom face central region 26. The thick region 27 projects outward (downward in FIGS. 3(A) to 4(B)) with respect to the bottom face central region 26 and the bottom face outer region 28. In a configuration that is not provided with the thick region 27, when an excessive load is applied to the elastic valve body 3 during the insertion or removal of the male connector 100 or when the male connector 100 is repeatedly attached and detached, longitudinal ends of the communicating slit 7, the longitudinal ends facing the bottom face 21, may disadvantageously be split. The thick region 27 reinforces the longitudinal ends and thereby enables the occurrence of the above problem to be prevented. In the present embodiment, when the elastic valve body 3 is viewed from the bottom face 21, the annular thick region 27 is formed in a manner to surround the slit 7 formed on the top face 20 and thickest at positions on the outer side in the longitudinal direction of the slit 7. Such a configuration makes it possible to prevent the ends of the slit 7 from being split and to ensure both an excellent insertability of the male connector into the elastic valve body 3 and maintenance of the elastic restoring force of the elastic valve body 3. A bottom face annular groove 29 is formed on the bottom face outer region 28 in a manner to surround the thick region 27. A locking projection 39 (described below) of the bottom face cap 16 enters the bottom face annular groove 29 and compresses the elastic valve body 3 to constitute a part of the holding section (refer to FIG. 5).

Figure 5:
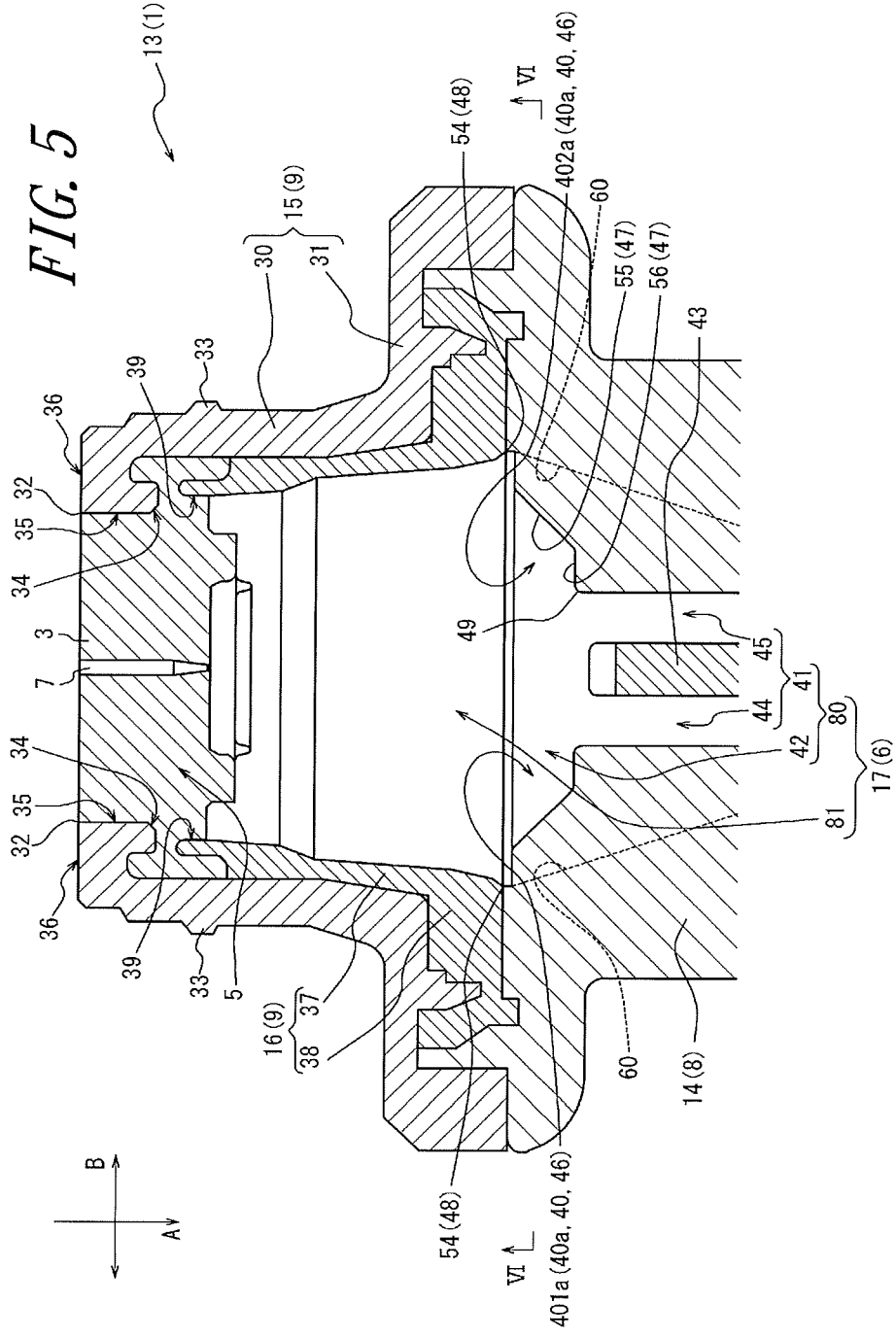
FIG. 5 is an enlarged sectional view of a branch port of the connector.

FIG. 5 is an enlarged sectional view of the branch port 13 in the connector 1 and illustrates a state in which the elastic valve body 3 is held between the top face cap 15 and the bottom face cap 16. The configurations of the top face cap 15, the bottom face cap 16, and the cap support section 14 will be described below with reference to FIG. 5.

As illustrated in FIG. 5, the top face cap 15 includes a substantially cylindrical hollow barrel 30 and a flange 31 which is formed on one end of the hollow barrel 30. As illustrated in FIG. 5, an edge 32 is located on an upper face (an upper face in FIG. 5) on the other end of the hollow barrel 30. The edge 32 forms one end of the insertion section 5 into which the male connector 100 is inserted from the outside and defines a substantially circular insertion port. A screw thread 33 is formed on the outer peripheral face of the hollow barrel 30 so as to be screwed with a lock connector defined by ISO 594. The flange 31 is a region integrally molded with the hollow barrel 30. The flange 31 is engaged with the cap support section 14 of the holder 8 (described below) so that the top face cap 15 is held by the cap support section 14.

As illustrated in FIG. 5, the locking projection 34 is formed on an inner wall of the hollow barrel 30 at a position near the edge 32. The locking projection 34 projects in the insertion direction A of the male connector 100 and enters the top face annular groove 24 of the elastic valve body 3 to compress the elastic valve body 3. The inner wall 35 formed between the edge 32 and the locking projection 34 has contact with the top face central region 22 of the elastic valve body 3 when the male connector 100 is not inserted and has contact with the male connector 100 when the male connector 100 is inserted (refer to FIG. 11). That is, when the male connector 100 is not inserted, the top face central region 22 is fitted into a space surrounded by the inner wall 35. On the other hand, when the male connector 100 is inserted, the male connector 100 is fitted with the top face cap 15 through the cylindrical inner wall 35. Although the inner wall 35 in the present embodiment has a cylindrical shape parallel to the insertion direction A, the inner wall 35 may have a tapered shape whose inner diameter is gradually reduced in the insertion direction A corresponding to the outer shape of the male connector 100.

The upper face of the hollow barrel 30 has the edge 32 and a planar extending section 36 which surrounds the edge 32. When the top face central region 22 of the elastic valve body 3 is fitted into the space surrounded by the inner wall 35, that is, when the male connector 100 is not inserted, the top face central region 22 of the elastic valve body 3 is housed up to the position (height) of the edge 32, and the top face central region 22 of the elastic valve body 3 and the extending section 36 of the top face cap 15 form the same plane. Accordingly, no step is formed between the top face central region 22 and the extending section 36. Thus, in a wiping operation for disinfection which is typically performed by a user immediately before the insertion of the male connector 100, the entire top face central region 22 can be easily wiped off. As a result, the valve body 3 can be maintained in a sanitary condition without various germs and foreign substances left therein.

As illustrated in FIG. 5, similarly to the top face cap 15, the bottom face cap 16 includes a substantially cylindrical hollow barrel 37 and a flange 38 which is formed on one end of the hollow barrel 37. The locking projection 39 is formed on the other end of the hollow barrel 37. The locking projection 39 projects in a direction opposite to the insertion direction A of the male connector 100 and enters the bottom face annular groove 29 of the elastic valve body 3 to compress and hold the elastic valve body 3 together with the locking projection 34 of the top face cap 15.

The bottom face cap 16 is ultrasonic-bonded to the inner face of the hollow barrel 30 and/or the lower face (the lower face in FIG. 5) of the flange 31 of the top face cap 15 and thereby held by the top face cap 15. Further, the position of the bottom face cap 16 is fixed by supporting the flange 38 of the bottom face cap 16 by the cap support section 14 (described below).

As illustrated in FIG. 5, the cap support section 14 of the holder 8 supports the top face cap 15 and the bottom face cap 16 and defines a part of the first flow path 17 (the flow path 6) inside thereof. The cap support section 14 of the present embodiment has direct contact with the top face cap 15 and the bottom face cap 16 to support both of them. Alternatively, for example, the cap support section 14 may have direct contact only with the bottom face cap 16 without having contact with the top face cap 15 and the top face cap 15 may have contact with the bottom face cap 16 so as to be supported by the bottom face cap 16. That is, the cap support section 14 may have direct contact with either the top face cap 15 or the bottom face cap 16 to support, and may not have direction contact with the other one. The members having direct contact with each other are preferably bonded to each other by, for example, ultrasonic bonding.

In the present embodiment, the top face cap 15 and the bottom face cap 16 hold the elastic valve body 3 therebetween to hold the elastic valve body 3 inside the insertion section 5. Alternatively, for example, the cap support section 14 and the bottom face cap 16 may be integrated, that is, the bottom face cap 16 may constitute a part of the holder 8.

In the present embodiment, when the male connector 100 is not inserted, the insertion section 5 communicates with the first flow path 17 defined by the bottom face cap 16 and the cap support section 14. When the male connector 100 is inserted into the connector 1, a tip 101 of the male connector 100 passes through the insertion section 5 and enters the inside of the first flow path 17. Accordingly, a liquid flow path inside the male connector 100 is brought to communicate with a cap support section flow path 80 of the first flow path 17 (the flow path 6), the cap support section flow path 80 being defined by the cap support section 14.

The cap support section flow path 80 defined by the cap support section 14 is a hollow section which connects a bottom face cap flow path 81 of the first flow path 17, the bottom face cap flow path 81 being defined by the bottom face cap 16, and an internal space of the substantially cylindrical holder main body 10 (refer to FIG. 1(A)) to each other in the insertion direction A of the male connector and is adjacent to a tip receiving section 40 which receives the tip 101 of the male connector 100 inserted from the outside. Specifically, the cap support section flow path 80 includes a holder main body side flow path 41 and a connection flow path 42. The holder main body side flow path 41 directly communicates with the internal space of the substantially cylindrical holder main body 10. The connection flow path 42 is located between the holder main body side flow path 41 and the bottom face cap flow path 81 in the insertion direction A of the male connector to connect the holder main body side flow path 41 and the bottom face cap flow path 81 to each other and is adjacent to the tip receiving section 40, which receives the tip 101 of the male connector 100 inserted from the outside through the slit 7 of the elastic valve body 3, in a direction B perpendicular to the insertion direction A. The tip receiving section 40 will be described in detail below.

As illustrated in FIG. 5, the cap support section 14 of the present embodiment is provided with a partition wall 43 which divides the holder main body side flow path 41 into two flow paths. Thus, the holder main body side flow path 41 includes an inflow path 44 which is located at a side corresponding to the upstream port 11 (refer to FIG. 1(A)) and an outflow path 45 which is located at a side corresponding to the downstream port 12 (refer to FIG. 1(A)) with the partition wall 43 interposed therebetween. The partition wall 43 will be described in detail below.

Figure 6:
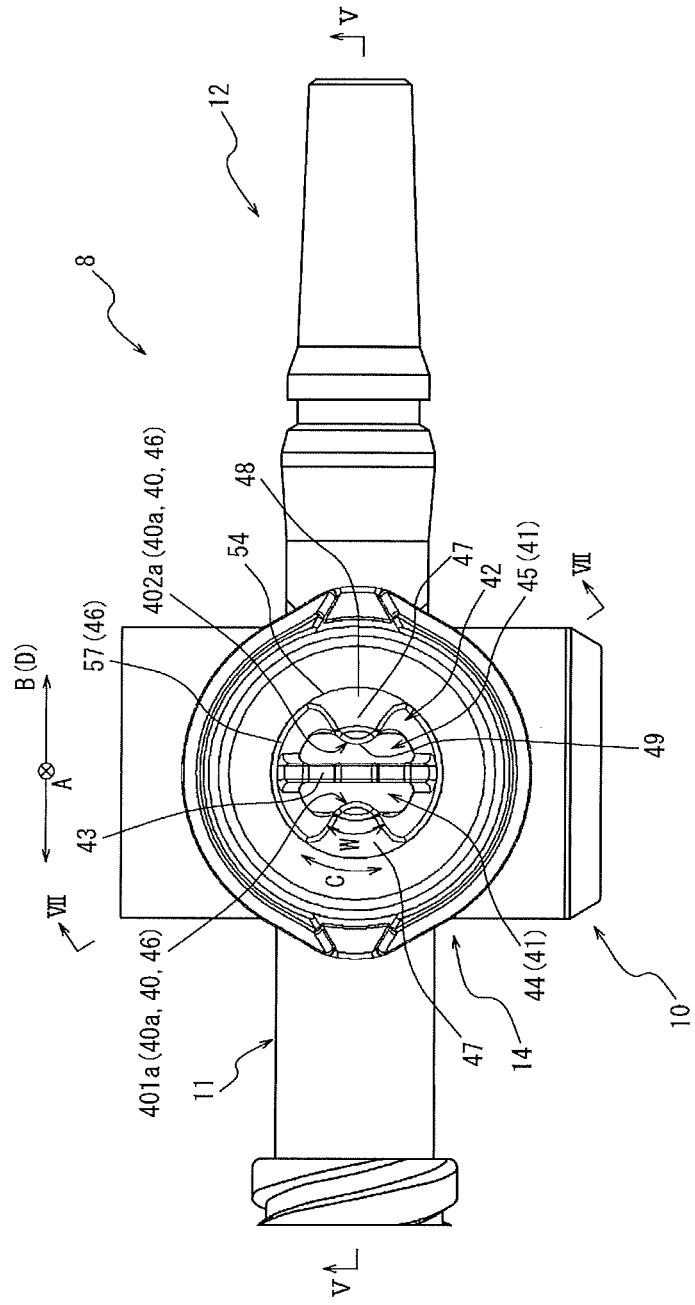
FIG. 6 is a diagram of a holder of the connector viewed in an insertion direction of a male connector.
Figure 7:
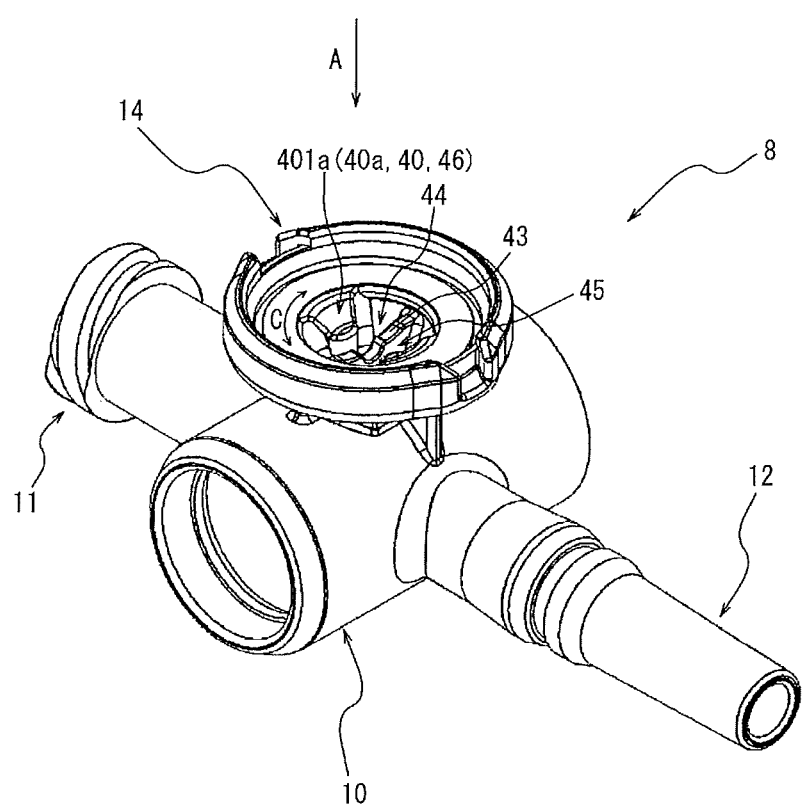
FIG. 7 is a perspective view of the holder of the connector.
Figure 8:
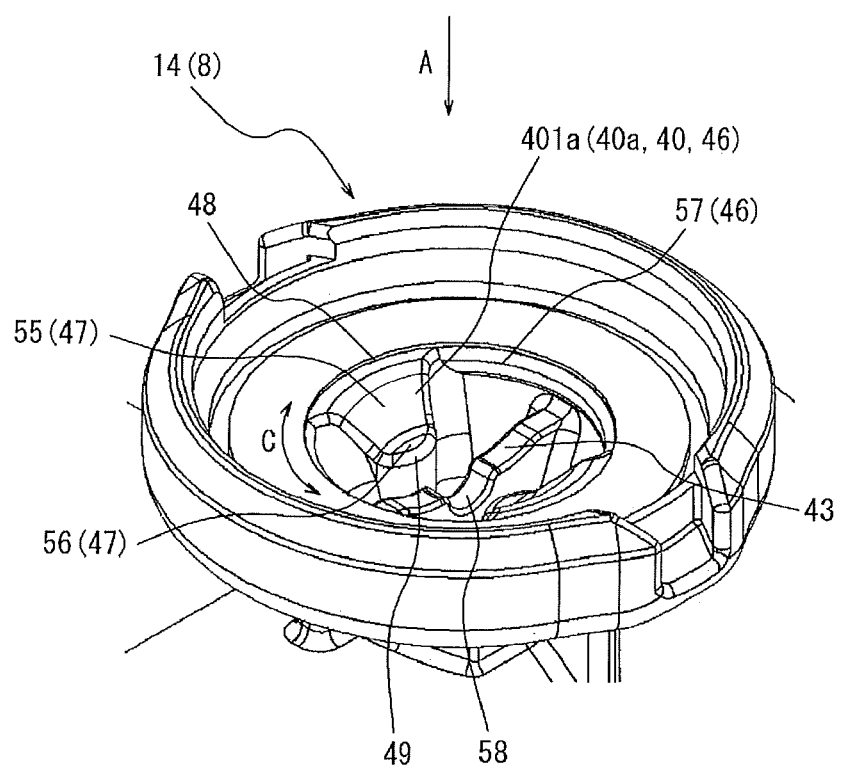
FIG. 8 is an enlarged perspective view of a cap support section shown in FIG. 7.

Next, the tip receiving section 40 formed on the cap support section 14 will be described. FIG. 6 is a diagram illustrating the holder 8 by itself, with the top face cap 15 and the bottom face cap 16 (refer to FIG. 1(B), for example) detached, viewed in the insertion direction A of the male connector. The cross section of the cap support section 14 illustrated in FIG. 5 is taken along line V-V in FIG. 6. FIG. 7 is a perspective view illustrating the entire holder 8. FIG. 8 is a perspective view illustrating the cap support section 14 of the holder 8. Hereinbelow, the tip receiving section 40 will be described in detail with reference to FIGS. 5 to 8.

As described above, the tip receiving section 40 receives the tip 101 of the male connector 100 inserted from the outside through the slit 7 of the elastic valve body 3 to thereby prevent the male connector 100 from being excessively inserted into the connector 1 in the insertion direction A of the male connector.

As illustrated in FIG. 5, the tip receiving section 40 is formed on an inner wall 46 which defines the connection flow path 42. As illustrated in FIGS. 6 to 8, when a circumferential direction of one cross section of the connection flow path 42 whose cross section perpendicular to the insertion direction A of the male connector has a substantially circular shape (in the present embodiment, a cross section of the connection flow path 42 on an end facing the elastic valve body 3, in other words, a cross section including an edge 54 illustrated in FIGS. 5 and 6 which defines one end of the connection flow path 42 on a face of the cap support section 14, the face facing the elastic valve body 3) is denoted by "C", the tip receiving section 40 is formed only on a part of the inner wall 46 which defines the connection flow path 42 in the circumferential direction C. That is, the tip receiving section 40 is formed only on a part of the inner wall 46 in a cross section that is perpendicular to the insertion direction A of the male connector and includes at least a part of the tip receiving section 40 (a cross section taken along line VI-VI in FIG. 5, for example), and not formed on the entire inner wall 46 in this cross section. That is, the tip receiving section 40 defines a contact area less than an entire circumference of the inner wall 46 defining the flow path 42. Further, in this cross section, the tip receiving section 40 is adjacent to the connection flow path 42 of the cap support section flow path 80. That is, a part surrounding the tip receiving section 40 in this cross section is a flow path for an infusion solution. As described below, part of the infusion solution is divided to flow on both sides of the tip receiving section 40.

In the present embodiment, the tip receiving section 40 is formed on the inner wall 46 which defines the cap support section flow path 80 of the first flow path 17. Alternatively, the tip receiving section 40 may be formed on the inner wall of the bottom face cap 16, the inner wall defining the bottom face cap flow path 81.

As illustrated in FIGS. 6 to 8, the tip receiving section 40 includes projections 40a which project toward the connection flow path 42 (in FIG. 6, also toward the holder main body side flow path 41) in the direction B perpendicular to the insertion direction A of the male connector when viewed in the insertion direction A of the male connector. More specifically, the tip receiving section 40 in the present embodiment includes parts of the inner wall 46 which define the connection flow path 42, the parts projecting toward the connection flow path 42 in the direction B when viewing the tip receiving section 40 in the insertion direction A. Thus, the inner wall 46 has the projections 40a and a circular arc section 57 which is continuous on both sides of each of the projections 40a in the cross section that is perpendicular to the insertion direction A of the male connector and includes at least a part of the projections 40a as the tip receiving section 40.

The tip receiving section 40 has a tip receiving face 47 which receives the tip 101 of the male connector 100 inserted from the outside. As illustrated in FIG. 5, the tip receiving face 47 of the present embodiment is a face of each of the projections 40a as the tip receiving section 40, the face facing the elastic valve body 3, and extends from a base 48 through an apex 49 of each of the projections 40a. Specifically, the tip receiving face 47 has a first extending section 55 and a second extending section 56. The first extending section 55 is a face that extends in such a manner that a projecting amount toward the connection flow path 42 in the direction B perpendicular to the insertion direction A (in the present embodiment, the length from the edge 54 in the direction B perpendicular to the insertion direction A) increases toward the insertion direction A of the male connector 100. That is, as shown for example in FIG. 5, the first extending section 55 extends in an inclined manner relative to the insertion direction A of the male connector and relative to the direction B perpendicular to the insertion direction. The second extending section 56 continuously extends up to the apex 49 on an end of the first extending section 55, the end being adjacent to the apex 49, and has a flat face perpendicular to the insertion direction A. FIG. 5 shows that the second extending section 56 is other than parallel to the first extending section 55. FIG. 5 also shows that the second extending section intersects the first extending section at an angle (i.e., an angle other than 180°). In the present embodiment, the tip 101 of the male connector 100 abuts against the first extending section 55 with the elastic valve body 3 interposed therebetween. This point will be described in detail below (refer to FIGS. 11 and 12).

In the present embodiment, both the first extending section 55 and the second extending section 56 are configured as planar faces. However, the first extending section 55 and the second extending section 56 are not limited to this configuration. For example, the first extending section 55 and/or the second extending section 56 may be configured as a circular arc face.

Each of the projections 40a has a shape that becomes gradually slimmer or narrower from the base 48 toward the apex 49 when viewed in the insertion direction A of the male connector. FIGS. 6-8 show that each projection 40a has a shape in which the projection gradually and continuously narrows from the base 48 to the apex 49. It is possible to prevent the area of the connection flow path 42 in the cross section perpendicular to the insertion direction A from being reduced by making the apex 49 slimmer than the base 48, that is, in the present embodiment, by reducing a width W in the circumferential direction C. In addition, it is possible to ensure the strength for receiving the tip 101 of the male connector 100 by making the base 48 thicker than the apex 49, that is, in the present embodiment, by increasing the width W in the circumferential direction C.

In the present embodiment, the outer shape of each of the projections 40a viewed in the insertion direction A of the male connector is a curved shape such as a sinusoidal curve and the apex 49 has a circular arc shape. However, the shapes of the projections 40a and the apex 49 are not limited to these shapes. For example, a shape having a part formed by a straight line may be employed.

Further, the plurality of projections 40a are formed in the circumferential direction C. In the present embodiment, as illustrated in FIG. 6, two projections 40a are formed to face each other across the connection flow path 42 in the direction B perpendicular to the insertion direction A. However, the number of projections 40a is not limited to two, and may be three or more, or even a single projection is possible. Although the two projections 40a in the present embodiment face each other across the connection flow path 42 in the direction B perpendicular to the insertion direction A, the projections 40a are not limited to this configuration. The projections 40a may be formed at positions that do not face each other across the connection flow path 42 in the direction B perpendicular to the insertion direction A.

In the present embodiment, due to the relationship with the partition wall 43 (described below), as illustrated in FIG. 6, the projections 40a face each other across the connection flow path 42 in a direction D from the upstream port 11 to the downstream port 12 in the direction B perpendicular to the insertion direction A. Specifically, as illustrated in FIG. 6, the projections 40a of the present embodiment have a configuration in which a first projection 401a located at a side corresponding to the upstream port 11 and the second projection 402a located at a side corresponding to the downstream port 12 face each other.

Figure 9:
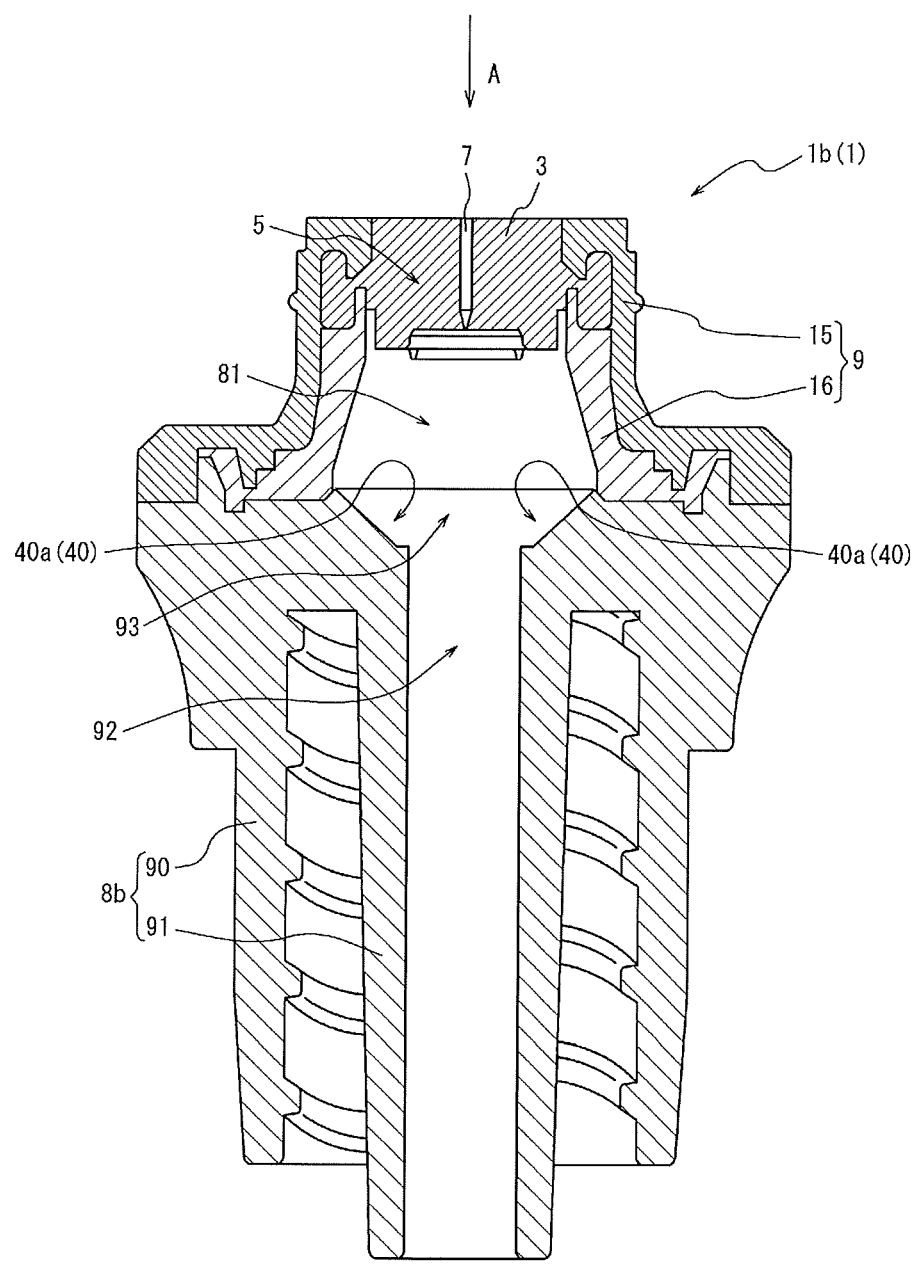
FIG. 9 is a diagram illustrating a modification of the connector.
Figure 10:
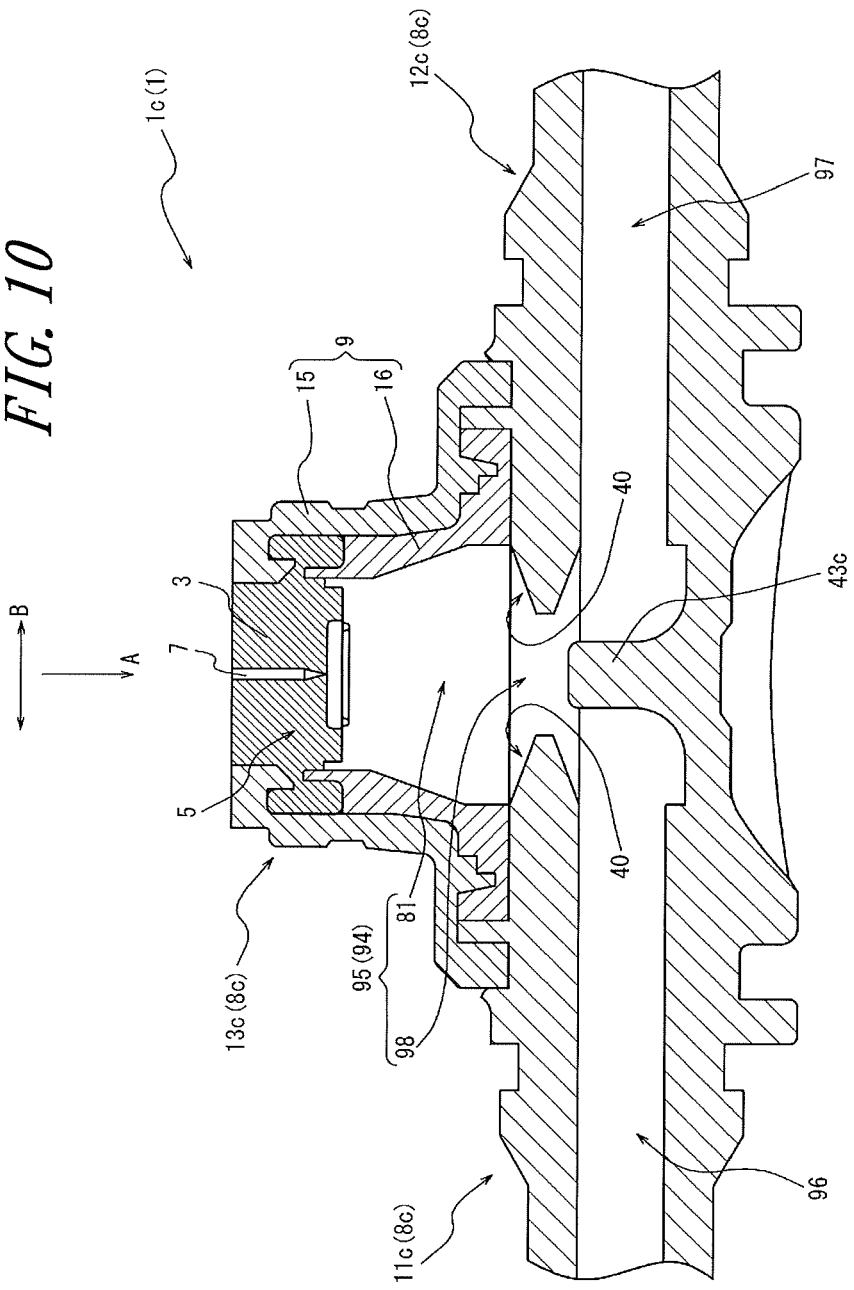
FIG. 10 is a diagram illustrating another modification of the connector.

In the present embodiment, the three-way stopcock 1a is described as the connector 1. However, the tip receiving section 40 is applicable not only to a three-way stopcock, but also to, for example, a linear connector 1b which has only a linear flow path as illustrated in FIG. 9 and a T-shaped connector 1c which has no cock and has a T-shaped flow path as illustrated in FIG. 10.

Specifically, the linear connector 1b differs from the three-way stopcock 1a in the exemplary embodiment of the disclosure mainly in the shape of a holder. The same elements as the elements of the three-way stopcock 1a are denoted by the same reference signs also in FIG. 9. A holder 8b of the linear connector 1b is provided with a substantially cylindrical barrel 90 which has a screw thread for a lock connector formed on the inner peripheral face thereof and a male luer section 91 which is formed on a hollow section of the barrel 90. An inner wall of the male luer section 91 in the holder 8b defines a substantially cylindrical flow path 92. The inner wall of the holder 8b defines a connection flow path 93 which connects the flow path 92 and the bottom face cap flow path 81 to each other. The inner wall of the holder 8b which defines the connection flow path 93 has a shape similar to the shape of the connection flow path 42 of the three-way stopcock 1a illustrated in FIGS. 5 to 8. The projections 40a as the tip receiving section 40 are formed on the inner wall of the holder 8b.

The T-shaped connector 1c differs from the three-way stopcock 1a in the exemplary embodiment of the disclosure mainly in that the T-shaped connector 1c has no cock and has a holder having a different shape due to the lack of a cock. The same elements as the elements of the three-way stopcock 1a are denoted by the same reference signs also in FIG. 10. A holder 8c of the T-shaped connector 1c is provided with a branch port 13c which holds the elastic valve body 3 and defines the flow path 94, and an upstream port 11c which is located on one side and a downstream port 12c which is located on the other side with the flow path 94 interposed therebetween in the direction B perpendicular to the insertion direction A of the male connector 100. When the flow path 94 is referred to as a first flow path 95, the upstream port 11c defines a substantially cylindrical second flow path 96 which communicates with the first flow path 95, and the downstream port 12c defines a substantially cylindrical third flow path 97 which communicates with the first flow path 95. The T-shaped connector 1c is provided with a partition wall 43c located between the second flow path 96 and the third flow path 97. The partition wall 43c guides an infusion solution toward the insertion section 5 when the infusion solution flows from the second flow path 96 to the third flow path 97 with the male connector 100 not inserted in the insertion section 5. The first flow path 95 includes a bottom face cap flow path 81 defined by the bottom face cap 16 and a holder flow path 98 defined by the holder 8c. The tip receiving section 40 which receives the tip 101 of the male connector 100 inserted from the outside is formed on the inner wall which defines the holder flow path 98. The tip receiving section 40 is formed only on a part of the inner wall of the holder 8c in a cross section that is perpendicular to the insertion direction A of the male connector and includes at least a part of the tip receiving section 40.

As described above, the tip receiving section 40 is applicable not only to the three-way stopcock 1a as the connector 1, but also to the linear connector 1b and the T-shaped connector 1c. Among these connectors, the tip receiving section 40 is particularly effectively used in the three-way stopcock 1a of the present embodiment or the T-shaped connector 1c which can be used as a part of a main line of the infusion line even when the male connector 100 is not inserted. This is because, in addition to a function of receiving the tip 101 of the male connector 100 when the male connector 100 is inserted, it is possible to contribute to the formation of turbulent flow of an infusion solution inside or near the bottom face cap flow path 81 of the first flow path 17 defined by the branch port 13 even when the male connector 100 is not inserted to wash away a nutrient or a liquid medicine stagnating near the inner wall of the bottom face cap 16 to thereby prevent the nutrient or the liquid medicine from stagnating as it is. A nutrient or a liquid medicine may stagnate inside the connector. In this case, for example, the nutrient may cause the propagation of bacteria inside the connector and is thus not preferred in view of sanitary. On the other hand, the liquid medicine may cause the occurrence of unexpected mixing with a different liquid medicine to be administered.

This point will be described in detail with reference to FIGS. 1(A) and 1(B), and 5 to 8. The projections 40a are adjacent to the connection flow path 42 of the first flow path 17 (the flow path 6) in the cross section that is perpendicular to the insertion direction A of the male connector 100 and includes at least a part of the projections 40a (the cross section taken along line VI-VI in FIG. 5, for example). More specifically, the connection flow path 42 of the first flow path 17 (the flow path 6) is located on both sides of each of the projections 40a in the circumferential direction C. In such a configuration, even when an infusion solution flows through the first flow path 17 (the flow path 6) of the branch port 13 with the male connector 100 not inserted, the projections 40a enable the flow of the infusion solution to be partially divided and joined inside the first flow path 17. Turbulent flow of the infusion solution can be generated by collision between the infusion solution and the projections 40a which occurs during the joining and/or the division of the flow.

The first projection 401a (refer to FIGS. 5 to 8) in the projections 40a in the present embodiment divides part of an infusion solution flowing from the inflow path 44 into the bottom face cap flow path 81 (refer to FIG. 5) into two directions. That is, part of the flow of the infusion solution flowing from the inflow path 44 to the bottom face cap flow path 81 is divided into a plurality of directions along an outer wall of the first projection 401a, and the divided flows flow to the bottom face cap flow path 81 through different routes. Then, the flows of the infusion solution temporarily divided by the first projection 401a are again joined together after passing through the first projection 401a. Thus, turbulent flow caused by the joining of the flows is formed inside or near the bottom face cap flow path 81. Further, part of the infusion solution flowing out from the bottom face cap flow path 81 to the outflow path 45 collides with the second projection 402a (mainly, the tip receiving face 47 of the second projection 402a). Thus, turbulent flow of the infusion solution can be formed also in this place.

That is, turbulent flow of the infusion solution can be formed inside or near the bottom face cap flow path 81 by the first projection 401a and the second projection 402a. Thus, for example, an infusion solution stagnating, for example, on the inner wall of the bottom face cap 16 or the bottom face of the elastic valve body 3 can be reduced.

Further, in the present embodiment, an infusion solution flowing through the flow path located on both sides in the circumferential direction C with respect to the first projection 401a flows into the bottom face cap flow path 81 toward the inner wall of the hollow barrel 37 in the bottom face cap 16. Specifically, an inner wall 60 of the cap support section 14 which defines the flow path located on both sides in the circumferential direction C of the first projection 401a when viewed in the VII-VII cross section illustrated in FIG. 6 is connected to the inner wall of the hollow barrel 37 so that no large step is formed at a connection portion between the inner wall of the cap support section 14 and the inner wall of the hollow barrel 37 when the bottom face cap 16 is attached (refer to FIG. 5). Such a configuration makes it possible to allow an infusion solution flowing into the bottom face cap flow path 81 to flow along the inner wall of the hollow barrel 37 and the bottom face of the elastic valve body 3 in either case when the branch port 13 is used facing upward (vertical direction) or sideways (horizontal direction). Although the VII-VII cross section differs from the cross section illustrated in FIG. 5, an inner wall of the cap support section 14 in the VII-VII cross section is indicated by a broken line in FIG. 5.

The flow path located on both sides in the circumferential direction C with respect to the second projection 402a has a configuration similar to the configuration of the flow path located on both sides in the circumferential direction C with respect to the first projection 401a. Such a configuration makes it possible to prevent an infusion solution from stagnating near the inner wall of the hollow barrel 37 to allow the infusion solution to smoothly flow out of the bottom face cap flow path 81 in either case when the branch port 13 is used facing upward (vertical direction) or sideways (horizontal direction). In particular, when the branch port 13 is used sideways (horizontal direction) and the above step is formed between the inner wall of the cap support section 14 which defines the flow path located on both sides in the circumferential direction C of the second projection 402a and the inner wall of the hollow barrel 37, an infusion solution is likely to be accumulated on the inner wall of the hollow barrel 37 due to the gravity. Thus, preventing the formation of a step as described above is effective.

As illustrated in FIG. 1(A), the partition wall 43 in the exemplary embodiment of the disclosure enables an infusion solution flowing from the second flow path 18 defined by the upstream port 11 to the third flow path 19 defined by the downstream port 12 to flow through the bottom face cap flow path 81 of the first flow path 17 defined by the branch port 13 when the male connector 100 (refer to FIG. 11) is not inserted in the branch port 13. When there is no partition wall 43, an infusion solution flowing into the first flow path 17 from the hollow section 53 defined by the holder main body 10 and the flow path switching section 51 of the cock 4 may not reach the bottom face cap flow path 81. The partition wall 43 enables an infusion solution flowing into the first flow path 17 to reliably reach the bottom face cap flow path 81. Thus, it is possible to prevent the infusion solution from stagnating around the bottom face cap flow path 81 of the first flow path 17.

As illustrated in FIG. 5, the partition wall 43 is a plate-like member which divides the holder main body side flow path 41 defined by the branch port 13 into two flow paths in the direction B perpendicular to the insertion direction A of the male connector 100 inserted into the branch port 13. As illustrated in FIG. 6, the partition wall 43 is held by the inner wall of the cap support section 14. As illustrated in FIGS. 1(A) and 5, the partition wall 43 separates the inflow path 44 through which an infusion solution flowing into the bottom face cap flow path 81 in the first flow path 17 from the second flow path 18 passes and the outflow path 45 through which an infusion solution flowing out from the bottom face cap flow path 81 to the third flow path 19 from each other. Although, in the present embodiment, as illustrated in FIG. 6, the cross sectional shape of the inflow path 44 and the outflow path 45 perpendicular to the insertion direction A of the male connector is a substantially rectangular shape, the cross sectional shape is not limited to this shape. Further, the partition wall 43 is not limited to a flat plate, and may be a plate-like member having a curved face.

In the exemplary embodiment, both the partition wall 43 and the projections 40a are used together. Using these two members together makes it possible to further prevent an infusion solution or a liquid medicine from stagnating on the inner wall of the bottom face cap 16 or the bottom face of the elastic valve body 3 when the male connector 100 is not inserted and is thus particularly effective.

When the male connector 100 is inserted and the tip 101 of the male connector 100 is received by the projections 40a as the tip receiving section 40, the tip 101 of the male connector 100 does not have contact with the partition wall 43. This point will be described below.

Next, the flow of an infusion solution inside the connector 1 when the male connector 100 is not inserted in the branch port 13 will be described with reference to FIG. 1(A). When the male connector 100 is not inserted in the branch port 13, the connector 1 constitutes a part of a main line of an infusion line.

As described above, the flow path switching section 51 of the cock 4 which defines the hollow section 53 together with the inner wall of the substantially cylindrical holder main body 10 is rotatably housed inside the holder main body 10. The branch port 13 which holds the elastic valve body 3 and defines the first flow path 17 communicatable with the hollow section 53, the upstream port 11 which defines the substantially cylindrical second flow path 18 communicatable with the hollow section 53, and the downstream port 12 which defines the substantially cylindrical third flow path 19 communicatable with the hollow section 53 are disposed on the outer wall of the holder main body 10. The connector 1 is capable of supplying liquid flowing in the second flow path 18 to the third flow path 19 through the hollow section 53 and the first flow path 17.

As indicated by an arrow in FIG. 1(A), when the male connector 100 is not inserted in the branch port 13, an infusion solution from an infusion solution bag flows from the second flow path 18 defined by the upstream port 11 to the third flow path 19 defined by the downstream port 12 through the first flow path 17 (the flow path 6). Specifically, as illustrated in FIG. 1(A) or 5, an infusion solution flows through the second flow path 18, the hollow section 53, the inflow path 44 of the holder main body side flow path 41 (a part of the cap support section flow path 80), and the connection flow path 42 (a part of the cap support section flow path 80) in this order and reaches the bottom face cap flow path 81. Then, the infusion solution that has reached the bottom face cap flow path 81 flows through the connection flow path 42 (a part of the cap support section flow path 80), the outflow path 45 of the holder main body side flow path 41 (a part of the cap support section flow path 80), the hollow section 53, and the third flow path 19 in this order while making contact with the inner wall of the bottom face cap 16 by the action of turbulent flow caused by the projections 40a.

In this manner, when the male connector 100 is not inserted in the branch port 13, the connector 1 constitutes a part of the main line of the infusion line and prevents an infusion solution from stagnating inside the branch port 13 by the projections 40a and the partition wall 43.

The connector 1 with the male connector 100 not inserted has been mainly described above. Hereinbelow, each member of the connector 1 when the male connector 100 is inserted in the branch port 13 of the connector 1 will be described.

Figure 11:
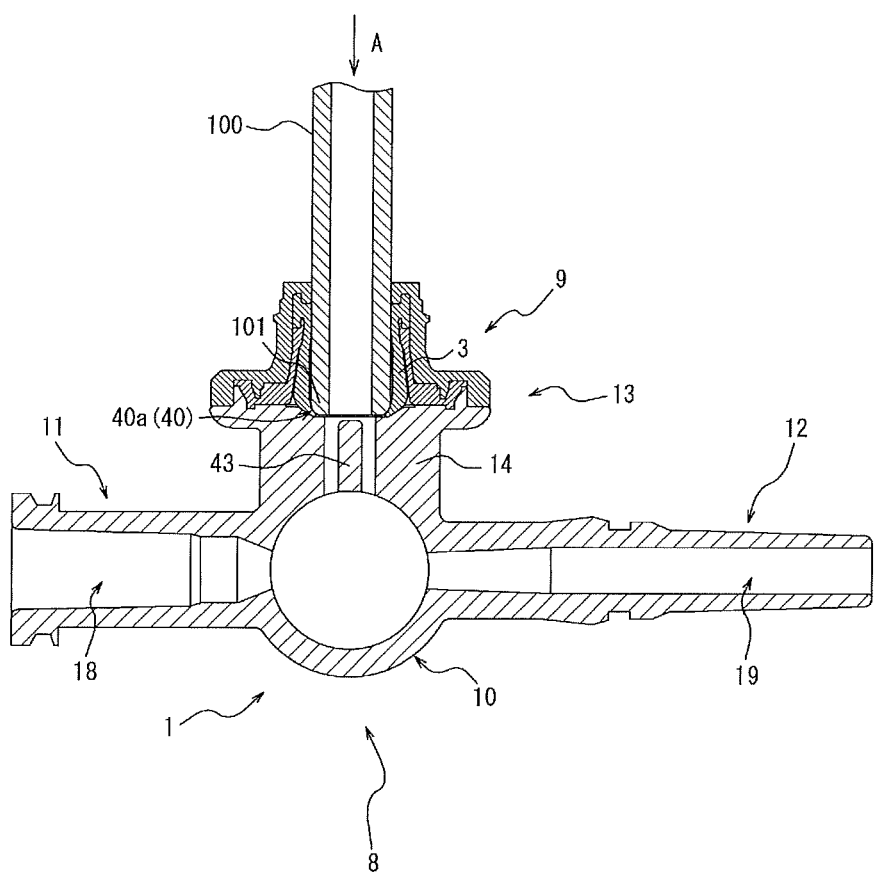
FIG. 11 is a sectional view of the connector with a male connector inserted.
Figure 12:
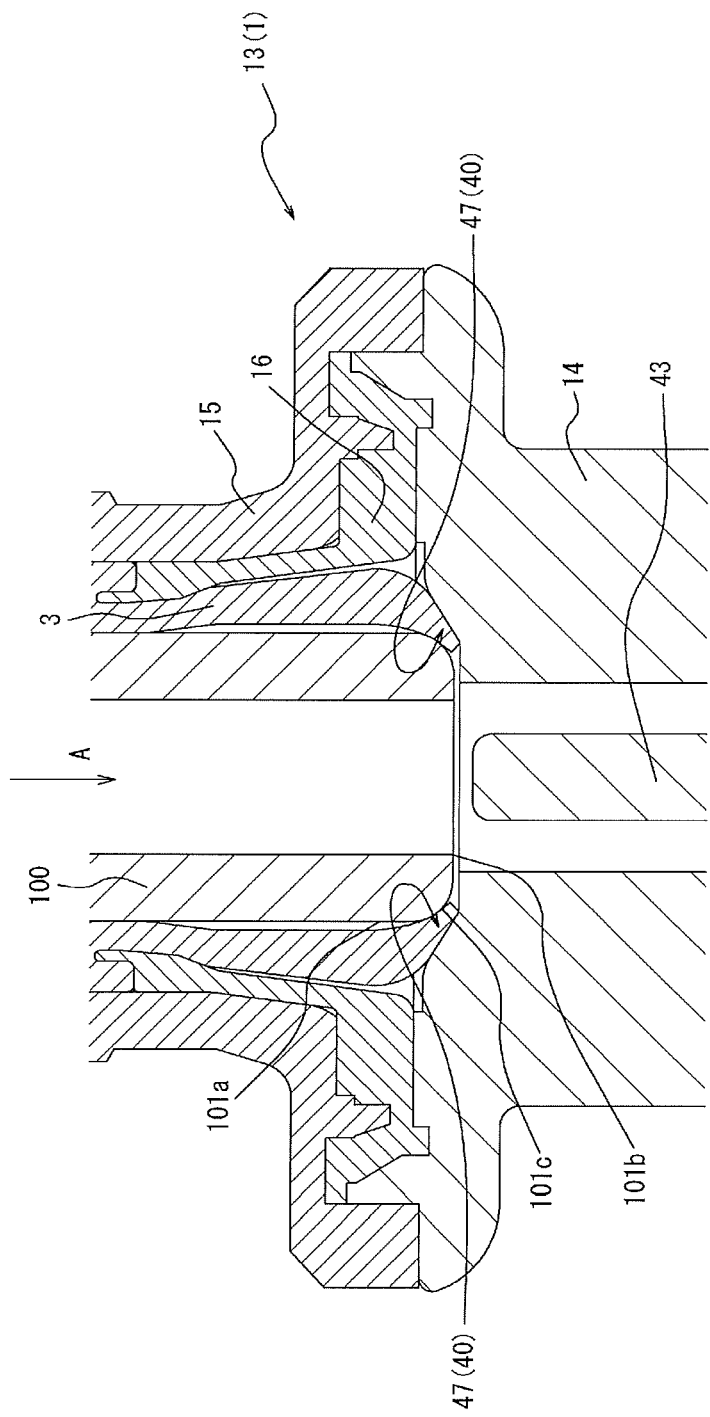
FIG. 12 is an enlarged sectional view of a tip of the male connector in FIG. 11.

FIG. 11 is a cross sectional view showing a state in which the male connector 100 is inserted in the branch port 13 of the connector 1. FIG. 12 is an enlarged sectional view near the tip 101 of the male connector 100 in the state of FIG. 11. For the convenience sake, FIG. 11 illustrates only the holder 8 and the cap 9 as the connector 1.

When the male connector 100 is inserted into the branch port 13 of the connector 1, the tip 101 of the male connector 100 pushes the elastic valve body 3 into the connector 1 to cause the elastic valve body 3 to elastically deform, and reaches the connection flow path 42 (refer to FIG. 5) inside the cap support section 14 through the penetrating slit 7.

The elastic valve body 3 elastically deforms by the insertion of the male connector 100 and enters a gap between the inner wall of the bottom face cap 16 and the outer wall of the male connector 100, so that the elastic valve body 3 is brought into intimate contact with the outer face of the male connector 100. Accordingly, leakage of liquid from the branch port 13 of the connector 1 to the outside is prevented.

The tip 101 of the male connector 100 abuts against the tip receiving section 40 formed on the inner wall of the cap support section 14 which defines the connection flow path 42 with the elastic valve body 3 interposed therebetween, so that the male connector 100 is positioned in the insertion direction A. More specifically, the tip 101 of the male connector 100 is provided with a tip peripheral face 101a which constitutes an outer wall in the direction B perpendicular to the insertion direction A of the male connector, a tip flat face 101b which defines an exit of the liquid flow path inside the male connector 100 and constitutes an outer wall in the insertion direction A of the male connector, and a tip curved face 101c which has a circular arc cross section connecting the tip peripheral face 101a and the tip flat face 101b to each other in the sectional view of FIG. 12. The tip curved face 101c of the tip 101 of the male connector 100 presses the tip receiving face 47 of the tip receiving section 40 through the elastic valve body 3. Accordingly, insertion of the male connector 100 in the insertion direction A is restricted, and the tip 101 of the male connector 100 is positioned in the insertion direction A.

In the exemplary embodiment of the disclosure, the tip curved face 101c of the male connector 100 is received by the first extending section 55 of the tip receiving face 47. Alternatively, the tip curved face 101c may be received by the second extending section 56. In the present embodiment, the tip receiving face 47 receives the tip curved face 101c of the male connector 100 through the elastic valve body 3. Alternatively, instead of or in addition to the tip curved face 101c of the male connector 100, the tip receiving face 47 may receive the tip peripheral face 101a or the tip flat face 101b. Further, in the present embodiment, the tip receiving section 40 receives the tip 101 of the male connector 100 through the elastic valve body 3. Alternatively, the tip receiving section 40 may have direct contact with any of the faces of the tip 101 of the male connector 100 without through the elastic valve body 3 to receive the tip 101.

As illustrated in FIGS. 11 and 12, the tip 101 of the male connector 100 and the partition wall 43 are not in contact with each other when the tip receiving section 40 receives the tip 101 of the male connector 100. That is, when the male connector 100 is received by the tip receiving section 40, a face of the partition wall 43, the face facing the elastic valve body 3, is located on the inner side of the connector 1 with respect to the tip receiving face 47 of the tip receiving section 40 so that the tip flat face 101b of the male connector 100 does not make contact with the partition wall 43. Such a configuration prevents the partition wall 43 from blocking a part of the exit of the liquid flow path of the male connector 100 even when, for example, a liquid medicine is supplied into the connector 1 from the liquid flow path of the inserted male connector 100. Thus, it is possible to reduce injection resistance of the liquid medicine supplied from the male connector 100.

Further, since the tip flat face 101b of the male connector 100 and the partition wall 43 are not in contact with each other, that is, a space is set between both of them, even when an infusion solution is allowed to flow from the upstream port 11 to the downstream port 12 through the first flow path 17 of the branch port 13 (refer to the arrow in FIG. 1(A)) with the male connector 100 as illustrated in FIGS. 11 and 12 connected to the branch port 13 of the connector 1, it is possible to ensure the flow amount of an infusion solution flowing from the upstream port 11 to the downstream port 12. Further, when the partition wall 43 is viewed in the direction D from the upstream port 11 to the downstream port 12, a cut-away section 58 having a circular arc shape (refer to FIG. 8) is formed on the face of the partition wall 43, the face facing the elastic valve body 3. The existence of the cut-away section 58 also contributes to ensuring the flow amount of an infusion solution.

Figure 13:
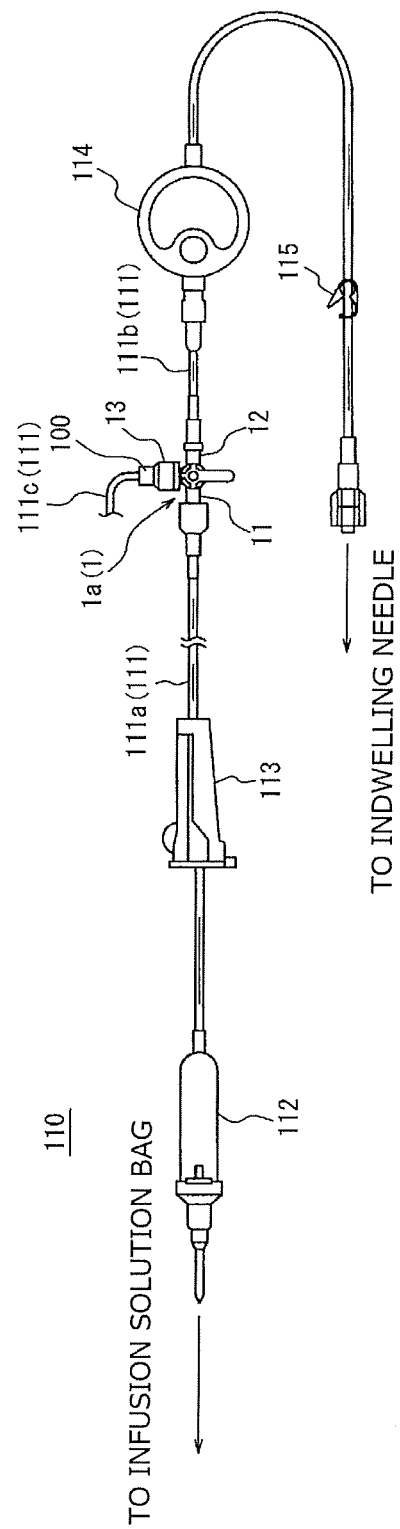
FIG. 13 is a diagram illustrating an infusion set provided with the connector according to an exemplary embodiment of the disclosure.

An infusion set 110 which is provided with the connector 1 as an embodiment of the present invention will be described. FIG. 13 is a diagram illustrating the infusion set 110. The infusion set 110 illustrated in FIG. 13 is provided with the three-way stopcock 1*a* as the connector 1. Alternatively, instead of the three-way stopcock 1*a*, the infusion set may be provided with the linear connector 1*b* or the T-shaped connector 1*c* described above. However, here, the infusion set 110 provided with the three-way stopcock 1*a* will be described for the convenience of description.

The infusion set 110 forms an infusion line that connects an infusion solution bag (not illustrated in FIG. 13) to an indwelling needle (also not illustrated in FIG. 13). Specifically, the infusion set 110 is provided with a plurality of infusion solution tubes 111, a drip infusion cylinder 112 through which the amount of an infusion solution supplied from the infusion solution bag is recognizable, a roller clamp 113 which adjusts the flow amount of an infusion solution inside the infusion solution tubes 111, an air vent filter 114 which discharges (or supplies) air present in the infusion line, and a clamp 115 which blocks the infusion solution tubes 111.

In the present embodiment, the three-way stopcock 1*a* as the connector 1 is disposed between the roller clamp 113 and the air vent filter 114. The connector 1 connects a first infusion solution tube 111*a* which extends to the downstream side from the drip infusion cylinder 112 and a second infusion solution tube 111*b* which extends on the upstream side of the air vent filter 114 so that liquid can flow therethrough to constitute a part of the flow path of the main line of the infusion line.

A third infusion solution tube 111*c* which is provided with the male connector 100 on the tip thereof is connected to the branch port 13 of the connector 1 to constitute a sub-line of the infusion line. Thus, the main line and the sub-line of the infusion line are connected to each other inside the connector 1.

In the present embodiment, the connector 1 is disposed between the roller clamp 113 and the air vent filter 114. However, the position of the connector 1 is not limited to this position, and the connector 1 may be disposed at a desired position. The infusion set 110 of the present embodiment is provided with only one connector 1. Alternatively, a plurality of connectors may be provided.

The disclosure herein relates to a connector that is capable of connecting thereto a male connector such as various medical devices and infusion solution containers and an infusion set provided with the connector.

The detailed description above describes a connector and an infusion set. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A connector comprising:
a housing defining an insertion section configured for a male connector to be inserted therein from outside and a flow path communicating with the insertion section; and
an elastic valve body having a slit and blocking the insertion section;
wherein the housing includes a tip receiving section formed on an inner wall defining the flow path, the tip receiving section configured for receiving a tip of the male connector inserted through the slit of the elastic valve body;
wherein the tip receiving section is formed on only a part of the inner wall in a cross section that is perpendicular to an insertion direction of the male connector such that the tip receiving section extends along less than an entire circumference of the inner wall defining the flow path;
wherein the tip receiving section comprises a plurality of projections projecting toward the flow path in a direction perpendicular to the insertion direction, each of the plurality of projections including a first side and a second side, each of the plurality of projections extending from a base of the projection to an apex of the projection in the direction perpendicular to the insertion direction and toward the flow path;
each of the projections gradually and continuously narrowing from the base of the projection to the apex of the projection; and
wherein the inner wall includes the plurality of projections and at least one circular arc section continuous between the first side of one of the plurality of projections and the first side of another of the plurality of projections in the cross section.
2. The connector according to claim 1, wherein the tip receiving section is adjacent to the flow path in the cross section.
3. The connector according to claim 1, wherein each of the plurality of projections includes a tip receiving face, the tip receiving face receiving the tip of the male connector, has an extending section extending in such a manner that a projecting amount toward the flow path in the direction perpendicular to the insertion direction increases toward the insertion direction.
4. The connector according to claim 1, wherein the housing includes a branch port holding the elastic valve body and defining the flow path, and an upstream port located on one side of the branch port and a downstream port located on the other side of the branch port with the flow path interposed therebetween in a direction perpendicular to the insertion direction of the male connector, and, when the flow path is defined as a first flow path, the upstream port defines a substantially cylindrical second flow path communicating with the first flow path and the downstream port defines a substantially cylindrical third flow path communicating with the first flow path.
5. The connector according to claim 1, wherein
the housing includes a substantially cylindrical holder main body, a cock defining a hollow section together with an inner wall of the holder main body is rotatably housed inside the holder main body, when the flow path is defined as a first flow path, a branch port holding the elastic valve body and defining the first flow path communicatable with the hollow section, an upstream port defining a substantially cylindrical second flow path communicatable with the hollow section, and a downstream port defining a substantially cylindrical third flow path communicatable with the hollow section are disposed on an outer wall of the holder main body, and the connector is capable of supplying liquid flowing in the second flow path to the third flow path through the hollow section and the first flow path.

6. The connector according to claim 4, wherein the housing includes a partition wall dividing the flow path defined by the branch port into two flow paths in the direction perpendicular to the insertion direction of the male connector inserted into the branch port, and the tip of the male connector and the partition wall are not in contact with each other when the tip receiving section receives the tip of the male connector.

7. The connector according to claim 1, wherein the tip receiving section receives the tip of the male connector through the elastic valve body.

8. An infusion set comprising the connector according to claim 1.

9. The connector according to claim 1, wherein the elastic valve body includes a top face and a bottom face, the slit not extending through the bottom face.

10. The connector according to claim 1, wherein each of said plurality of projections defines a tip receiving face configured to abut the tip of the male connector.

11. The connector according to claim 10, wherein the tip receiving face includes a first extending section and a second extending section.

12. The connector according to claim 1, wherein the connector comprises a stopcock connector.

13. The connector according to claim 1, wherein the connector comprises a T-connector.

14. The connector according to claim 1, wherein the connector comprises an inline connector.

15. A connector comprising:

a housing defining an insertion section configured for a male connector to be inserted therein from outside and a flow path communicating with the insertion section; and an elastic valve body having a slit and blocking the insertion section;

the housing including a tip receiving section formed on an inner wall defining the flow path, the tip receiving section configured for receiving a tip of the male connector inserted through the slit of the elastic valve body;

the tip receiving section being formed on only a part of the inner wall in a cross section that is perpendicular to an insertion direction of the male connector such that the tip receiving section extends along less than an entire circumference of the inner wall defining the flow path;

the tip receiving section comprising a plurality of projections projecting toward the flow path in a direction perpendicular to the insertion direction, each of the plurality of projections including a first side and a second side;

the inner wall including the plurality of projections and at least one circular arc section continuous between the first side of one of the plurality of projections and the first side of another of the plurality of projections in the cross section;

each of the plurality of projections possessing a tip receiving face which receives the tip of the male connector when the male connector is inserted through the slit of the elastic valve body, the tip receiving face extending from a base of the projection to an apex of the projection;

the tip receiving face of each projection comprising a first extending section and a second extending section, the first extending section of each projection extending radially inwardly in a direction away from the inner wall of the housing so that the radially inwardly extending first extending section extends from the base of the projection to the second extending section, the tip receiving face of the second extending section of each projection facing towards the elastic valve body, the second extending section of each projection extending radially inwardly in a direction away from the inner wall of the housing so that the second extending section extending radially inwardly extends from the first extending section to the apex of the projection, the second extending section of each projection intersecting the first extending section of the respective projection at an angle; and the first extending section of each projection and the elastic valve body being configured so that when the male connector is inserted through the slit of the elastic valve body, the tip of the male connector abuts against the first extending section with a portion of the elastic valve body interposed between the first extending section of each projection and the tip of the male connector.

16. The connector according to claim 15, wherein the second extending section of each projection is perpendicular to the insertion direction of the male connector.

17. A connector comprising:

a housing defining an insertion section configured for a male connector to be inserted therein from outside and a flow path communicating with the insertion section; and an elastic valve body having a slit and blocking the insertion section;

the housing including a tip receiving section formed on an inner wall defining the flow path, the tip receiving section configured for receiving a tip of the male connector inserted through the slit of the elastic valve body;

the tip receiving section being formed on only a part of the inner wall in a cross section that is perpendicular to an insertion direction of the male connector such that the tip receiving section extends along less than an entire circumference of the inner wall defining the flow path;

the tip receiving section comprising a plurality of projections projecting toward the flow path in a direction perpendicular to the insertion direction, each of the plurality of projections including a first side and a second side;

the inner wall including the plurality of projections and at least one circular arc section continuous between the first side of one of the plurality of projections and the first side of another of the plurality of projections in the cross section;

each of the plurality of projections possessing a tip receiving face which receives the tip of the male connector when the male connector is inserted through the slit of the elastic valve body, the tip receiving face extending from a base of the projection to an apex of the projection;

the tip receiving face of each projection comprising a first extending section and a second extending section, the first extending section of each projection extending radially inwardly in a direction away from the inner wall of the housing so that the radially inwardly extending first extending section extends between the base of the projection and the second extending section of the projection, the second extending section of each projection facing towards the elastic valve body and extending radially inwardly in a direction away from the inner wall of the housing so that the second extending section facing towards the elastic valve body and extending radially inwardly extends from the first extending section of the projection to the apex of the projection;

the first extending section extending in an inclined manner relative to the insertion direction of the male connector and relative to the direction perpendicular to the insertion direction so that a projecting amount of the first extending section toward the flow path in the direction perpendicular to the insertion direction increases toward the insertion direction of the male connector;

the second extending section being other than parallel to the first extending section; and the first extending section of each projection and the elastic valve body being configured so that when the male connector is inserted through the slit of the elastic valve body, the tip of the male connector abuts against the first extending section with a portion of the elastic valve body interposed between the first extending section of each projection and the tip of the male connector.

18. The connector according to claim 17, wherein the second extending section of each projection is perpendicular to the insertion direction of the male connector.

* * * * *